United States Patent
Schwartz et al.

(10) Patent No.: US 6,306,159 B1
(45) Date of Patent: *Oct. 23, 2001

(54) MENISCAL REPAIR DEVICE

(75) Inventors: Herbert E. Schwartz, Fort Wayne; Thomas C. May, Winona Kale, both of IN (US); Stuart Fromm, Rapid City, SD (US); Robert-Jan Enzerink, Davis; Eric Hubbard, Modesto, both of CA (US); John Margetts, Bountiful, UT (US); Keith Denlinger; David Cox, both of Warsaw, IN (US)

(73) Assignee: DePuy Orthopaedics, Inc., Warsaw, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/464,809

(22) Filed: Dec. 17, 1999

Related U.S. Application Data

(60) Provisional application No. 60/113,548, filed on Dec. 23, 1998.

(51) Int. Cl.[7] ..................................... A61B 17/04
(52) U.S. Cl. ............................. 606/232; 606/148
(58) Field of Search ..................... 606/232, 148, 606/72, 75

(56) References Cited

U.S. PATENT DOCUMENTS

| | | | |
|---|---|---|---|
| Re. 34,021 | 8/1992 | Mueller et al. | 606/232 |
| 4,669,473 | 6/1987 | Richards et al. | 606/232 |
| 4,741,330 | 5/1988 | Hayhurst | 606/232 |
| 4,750,492 | 6/1988 | Jacobs | 606/232 |
| 4,976,715 | 12/1990 | Bays et al. | 606/232 |
| 5,269,809 * | 12/1993 | Hayhurst et al. | 606/232 |
| 5,320,633 | 6/1994 | Allen et al. | |
| 5,520,691 * | 5/1996 | Branch | 606/72 |
| 5,626,614 | 5/1997 | Hart | |
| 5,725,556 * | 3/1998 | Moser et al. | 606/232 |
| 5,861,004 * | 1/1999 | Kensey et al. | 606/213 |
| 5,954,747 | 9/1999 | Clark | |
| 6,010,525 * | 1/2000 | Bonutti et al. | 606/232 |

FOREIGN PATENT DOCUMENTS 0 632 999 A1  6/1994 (EP).

OTHER PUBLICATIONS

O'Meara, Patrick. "The Basic Science of Meniscus Repair," Orthopaedic Review, Jun. 1993, pp. 681–686.
Clearfix Screw Advertisement, 1998. Innovasive Devices, Inc.
Winters and Justin, "Clearfix Meniscal Screw," Innovasive Devices, Inc. 1998.
Surgical Dynamics, Meniscal Stapler Advertisement, 1997.
Bionix Implants, Meniscus Arrow Advertisement, 1996.
Instrumennt Makar, Inc., Meniscus Mender II, 1989.
William G. Clancy, Jr., M.D., and Ben K. Graf, M.D., "Arthroscopic Mensical Repair," ACUFEX Microsurgical, Inc. Advertisement, 1988.

* cited by examiner

*Primary Examiner*—Gary Jackson
(74) *Attorney, Agent, or Firm*—Barnes & Thornburg

(57) ABSTRACT

The invention disclosed is a device for repairing a soft tissue defect, particularly a defect in the meniscus of a knee. The device comprises an outer wall anchor for engaging against an outside wall of the meniscus on a first side of the defect, an inner meniscal anchor engaging an inner surface of the meniscus on a second side of the defect, the inner meniscal anchor having a locking mechanism, and a suture adjustably connecting the outer wall anchor to the inner meniscal anchor. Tension on the suture pulls the defect together and the locking mechanism then locks the suture in place.

31 Claims, 4 Drawing Sheets

MENISCAL REPAIR DEVICE

This application claims priority under 35 U.S.C. § 119(e) to U.S. Provisional Application No. 60/113,548, filed Dec. 23, 1998, which is expressly incorporated by reference herein.

FIELD OF THE INVENTION

The present invention relates to a device for repairing a soft tissue defect or securing soft tissue to bone. More particularly, the present invention relates to a device for repairing a defect in the meniscus of the knee. The present invention also relates to a method for using the device to repair a defect in the meniscus.

BACKGROUND AND SUMMARY OF THE INVENTION

It is known in the art to repair defects in the meniscus of the knee. The meniscus rests on the tibial platform and extends about the perimeter of the platform. Menisci create concave surfaces which provide increased surface area for contact with the femoral condyles. This increased surface area is important for transmittal of loads across the tibio-femoral joint. Damaged menisci may be removed. However, removal may result in degenerative changes in the joint. Prior art devices for repairing torn menisci include arrows which are pushed into the meniscus, screws, and staples.

The meniscal repair device of the present invention comprises an outer wall anchor, an inner meniscal anchor, and a suture or tether which connects the anchors together. The suture may be tensioned to pull the outer and inner walls of the meniscus together, in order to close a defect.

The outer wall anchor may be longitudinally shaped and have one or more holes through which sutures may pass freely. The inner meniscal anchor preferably is shaped to resist forward and reverse movement once deployed. Also, the inner meniscal anchor may be cannulated to allow a suture to slide within. Once deployed, a suture loops through the outer wall anchor and both ends of the suture traverse back through the cannula of the inner meniscal anchor. The outer wall anchor acts as an anchor against the outer meniscal wall and as a pulley for the suture to pull through for tightening. After the anchors are satisfactorily placed, the two strands of suture may be tied or locked within the inner meniscal anchor by a variety of mechanisms. Because the suture length need not be fixed until insertion is complete, the device of this invention provides flexibility in placement within the meniscus, while enabling a surgeon to pull closed the defect in the meniscus.

In an alternative embodiment, the suture loops through the outer wall anchor and one end of the suture traverses back through the cannula of the inner meniscal anchor while the other end of the suture loops back to and is permanently attached to the inner meniscal anchor. When the device is properly positioned, the single suture strand may be locked into place.

The inner meniscal anchor may take a variety of shapes, including bullet-shaped with a wide base, bullet-shaped with fins, and flared. The inner meniscal anchor may also have a variety of locking devices, including a locking ring, wedge, snap groove, or laminated sheets. Preferably, the inner meniscal anchor will seat within the meniscus, adjacent to the inner meniscal wall. Such a placement provides proper support for the suture to close the tear in the meniscus. Also, because the inner meniscal anchor seats within the meniscal tissue, it does not interfere with tibio-femoral articulation.

The device of this invention can be used to repair a variety of soft tissue defects, for instance defects in tendon. Additionally, the device of this invention can also be used to attach soft tissue, such as tendon, to bone. Thus, while the present disclosure describes embodiments of this invention for use in the repair of a defect to a meniscus, it is understood that the device of this invention is suitable for many applications involving soft tissue.

In the method of this invention, the outer wall anchor is placed within a cannulated needle. The cannulated needle may have a slot, and the inner meniscal anchor may be located outside of the needle. The needle is then inserted through the meniscus, and a push rod deploys the outer wall anchor outside of the meniscus. With tension on the suture, the outer wall anchor flips into place, providing support against the outer rim wall of the meniscus. A second push rod may be used to push the inner meniscal anchor into a passageway in the meniscus which was created by the needle. Once the anchors are satisfactorily place, the suture is tightened, and may be secured by a variety of means. Arthroscopic techniques and needle placement are known in the art. See, e.g., U.S. Pat. No. 5,320,633, hereby incorporated by reference.

The outer wall anchor and inner meniscal anchor may be made of biocompatible material such as stainless steel, titanium, cobalt chrome, and polyethylene. Preferably, biodegradable materials may also be used, including poly lactic acid and poly lactic-glycolic acid. Other biodegradable materials are known. See, e.g., U.S. Pat. No. 4,976,715, hereby incorporated by reference. The suture may be made of resorbable or non-resorbable material.

Thus, in one embodiment of this invention a device is provided for repairing a soft tissue defect. The device comprises an outer wall anchor, an inner anchor having a locking mechanism, and a suture, wherein the suture adjustably connects the outer wall anchor to the inner anchor and the locking mechanism secures the suture to the inner anchor.

In another embodiment of this invention a device is provided for anchoring soft tissue to bone. The device comprises a bone anchor, a soft tissue anchor having a locking mechanism, and a suture, wherein the suture adjustably connect the bone anchor to the soft tissue anchor and the locking mechanism secures the suture to the soft tissue anchor.

In still another embodiment of this invention a device is provided for repairing a defect in a meniscus of a knee. The device comprises an outer wall anchor for engaging against an outside wall of the meniscus on a first side of the defect, an inner meniscal anchor engaging an inner surface of the meniscus on a second side of the defect, the inner meniscal anchor having a locking mechanism, and a suture adjustably connecting the outer wall anchor to the inner meniscal anchor. Tension on the suture pulls the outer wall anchor toward the inner meniscal anchor, thereby pulling the first and second sides of the defect together to close the defect. The locking mechanism then locks the suture in place.

In one more embodiment of this invention, a method for repairing the meniscus of a knee is provided. The method employs a meniscal repair device comprising an outer wall anchor for engaging against an outside wall of the meniscus on a first side of the defect; an inner meniscal anchor for engaging an inner surface of the meniscus on a second side of the defect, the inner meniscal anchor having a locking mechanism; and a suture adjustably connecting the outer wall anchor to the inner meniscal anchor. The method also employs a cannulated needle having a push rod. The outer wall anchor is placed within the cannulated needle, the cannulated needle is inserted into the meniscus from an inner surface of the meniscus, through the defect, to the outside wall of the meniscus, the outer wall anchor is deployed with the push rod, the inner meniscal anchor is pushed into the inner surface of the meniscus, the suture is tensioned to pull the first and second sides of the defect together, and the suture is locked in place with the locking mechanism.

Additional features of the present invention will become apparent to those skilled in the art upon consideration of the following detailed description of preferred embodiments exemplifying the best mode of carrying out the invention as presently perceived.

DETAILED DESCRIPTION OF THE DRAWINGS

Figure 1:
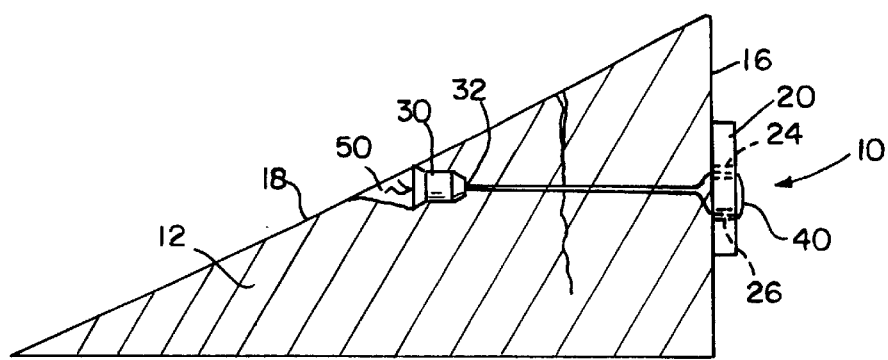
FIG. 1 is a cross-section of a damaged meniscus with a meniscal repair device of this invention.

FIG. 1 shows generally a cross-section of a meniscus 12 showing an embodiment of meniscal repair device 10 of this invention. The meniscal repair device 10 comprises outer wall anchor 20, inner meniscal anchor 30, and suture 40. Outer wall anchor 20 is located adjacent to outer wall 16 of meniscus 12. Inner meniscal anchor 30 and much of suture 40 are contained within a passageway 50, which was made by an insertion needle (FIGS. 14, 15) when outer wall anchor 20 was deployed. Inner meniscal anchor 30 is buried just inside of passageway 50, adjacent to inner edge 18 of meniscus 12. Suture 40 connects outer wall anchor 20 and inner meniscal anchor 30. As suture 40 tightens, outer wall anchor 20 acts as a pulley. Suture 40 pulls defect 14 together. By tensioning the suture, the surgeon can close the defect, thereby promoting healing of the meniscus.

Figure 2:
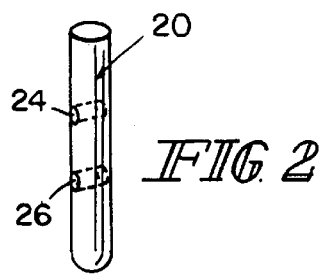
FIG. 2 is a side view of an outer wall anchor.
Figure 2A:
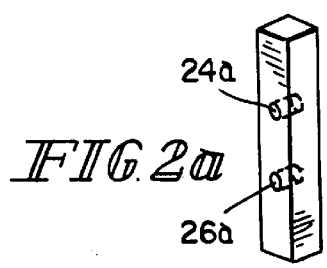
FIG. 2a is an alternative embodiment of an outer wall anchor.
Figure 2B:
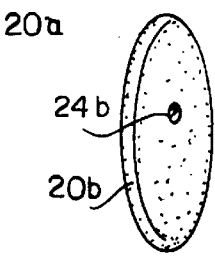
FIG. 2b is another alternative embodiment of an outer wall anchor.

Referring now to FIG. 2, an outer wall anchor 20 may be longitudinally shaped and has a first hole 24 and a second hole 26. As can be seen in FIG. 1, suture 40 passes freely through first hole 24 and loops through second hole 26, and both ends of the suture 40 extend through passageway 50 to inner meniscal anchor 30. FIG. 2a illustrates an alternative embodiment, showing outer wall anchor 20a. While outer wall anchor 20a is squared off, it still has two holes 24a and 26a through which a suture may pass. FIG. 2b shows another alternative embodiment for an outer wall anchor. Outer wall anchor 20b, as shown, is shaped like an elongated torus. As shown, outer wall anchor 20b has a single hole 24b. In use, the suture would exit from passageway 50, pass through hole 24b, and loop back through passageway 50. In a preferred embodiment, hole 24b is located off-center. This off-center placement promotes pulley action. Other shapes for outer wall anchor 20 are within the scope of this invention.

Figure 3:
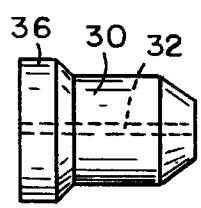
FIG. 3 is a side view of an inner meniscal anchor.

FIG. 3 illustrates an embodiment of inner meniscal anchor 30. Inner meniscal anchor 30 is designed to be inserted into passageway 50, but to wedge into place adjacent to the insertion point. Inner meniscal anchor 30 is provided with a wider base 36 to accomplish this wedging action. In a preferred embodiment, inner meniscal anchor 30 is also provided with a cannula 32, through which one or both ends of suture 40 may pass.

Figure 3A:
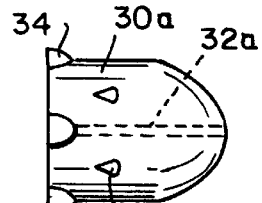
FIG. 3a is a an alternative embodiment of an inner meniscal anchor.
Figure 3B:
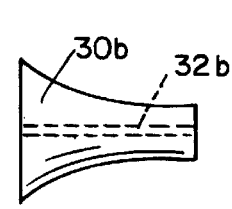
FIG. 3b is another alternative embodiment of an inner meniscal anchor.
Figure 4:
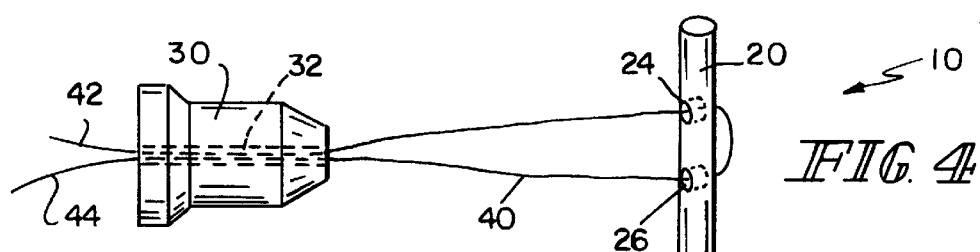
FIG. 4 is an embodiment of this invention, showing the combination of the outer wall anchor of FIG. 2, the inner meniscal anchor of FIG. 3, and a suture.
Figure 5:
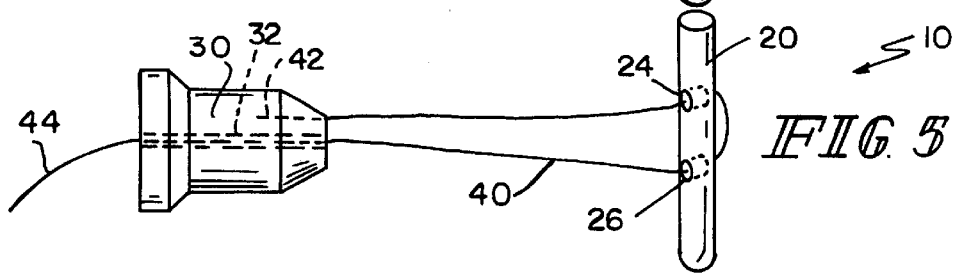
FIG. 5 is an alternative embodiment of FIG. 4.

FIGS. 3a and 3b illustrate several alternative embodiments of inner meniscal anchor 30. FIG. 3a illustrates a bullet-shaped inner meniscal anchor 30a. Inner meniscal anchor 30a is provided with fins 34 for digging into the sides of passageway 50 and for locking into place. FIG. 3b shows a flared embodiment of inner meniscal anchor 3b. Once properly placed, each embodiment provides a mechanism for stopping inner meniscal device 30 from moving in meniscus 12 toward defect 14. As with inner meniscal anchor 30, inner meniscal anchors 30a and 30b are provided with cannulae 32a and 32b, respectively FIGS. 4 and 5 illustrate two embodiments of the meniscal repair device 10 design. In FIG. 4, suture 40 loops through first and second holes 24, 26 of outer wall anchor 20, and first and second ends 42, 44 of suture 40 pass through cannula 32 of the inner meniscal anchor. First and second ends 42, 44 may be secured by a variety of means once the meniscal repair device 10 is properly inserted into meniscus 12 and suture 40 is tightened. In FIG. 5, first end 42 may be permanently attached to inner meniscal anchor 30. Suture 40 loops through first and second holes 24, 26 of outer wall anchor 20, and second end 44 passes back through cannula 32. As with the embodiment shown in FIG. 4, second end 44 may be secured by a variety of means once meniscal repair device 10 is properly seated and suture 40 is tightened. As shown in FIGS. 4 and 5, suture 40 passes through both holes 24, 26 of outer wall anchor 20. However, it is understood that with alternative configurations of the outer wall anchor suture 20 may pass through only one hole or may simply wrap around the outer wall anchor.

Figure 6:
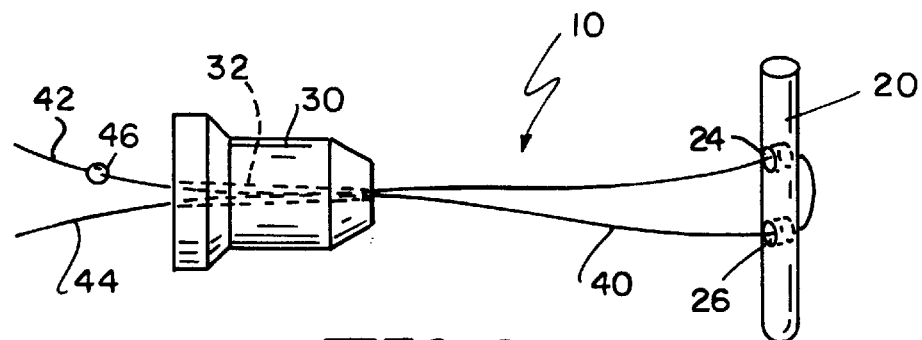
FIG. 6 is similar to FIG. 4, but showing one method of tightening and holding the sutures.
Figure 7:
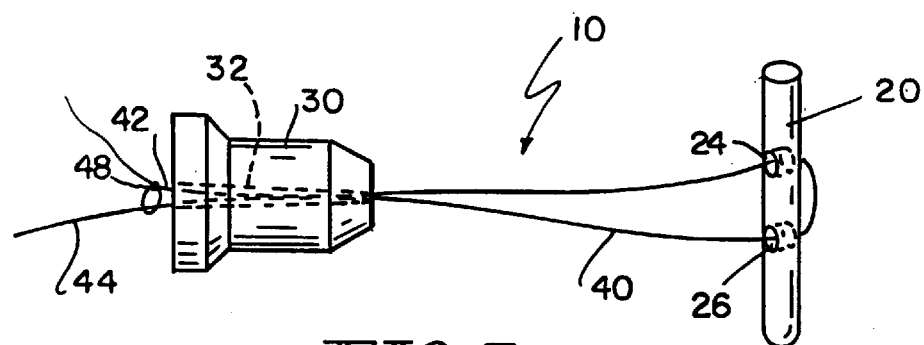
FIG. 7 is an alternative embodiment of FIG. 6.

Turning now to FIGS. 6 through 13, several embodiments for securing the sutures are illustrated. In FIGS. 6 and 7, the cannula 32 of inner meniscal anchor 30 is tapered or stepped. In FIG. 6, knot or bead 46 is placed on first end 42 of suture 40. Suture 40 passes through cannula 32 and loops through first and second holes 24, 26 of outer wall anchor 20, and then returns through cannula 32. Second end 44 can then be pulled so that bead 46 enters tapered or stepped cannula 32. As the surgeon continues to pull on the second end 44, the two ends 42, 44 of suture 40 wedge into cannula 32.

In FIG. 7, first end 42 includes a looped slip knot 48. Second end 44 may be fed through slip knot 48, and slip knot 48 may be slightly tightened against second end 44. As second end 44 is tensioned, slip knot 48 travels along second end 44, until slip knot 48 enters tapered or stepped cannula 32. Slip knot 48 may then push inner meniscal anchor 30 into meniscus 12. When inner meniscal anchor 30 is in position, slip knot 48 becomes locked onto second end 44 and slip knot 48 becomes wedged within tapered or stepped cannula 32.

Figure 8:
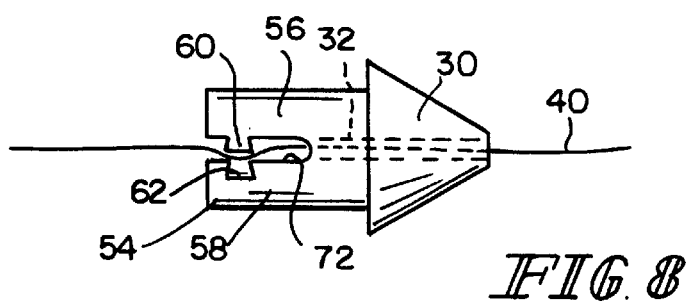
FIG. 8 is a cross section of an embodiment of the inner meniscal anchor having a snap groove.

FIG. 8 illustrates an embodiment employing a snap groove. In this embodiment, rear section 58 of inner meniscal anchor 30 is provided with a split gap 72 which splits the rear section 58 into upper section 56 and lower section 54. A tooth 60 is provided on upper section 56, while a matching groove 62 is provided on lower section 54. When the tooth 60 and groove 62 are locked together, suture 40 is captured there between.

Figure 9:
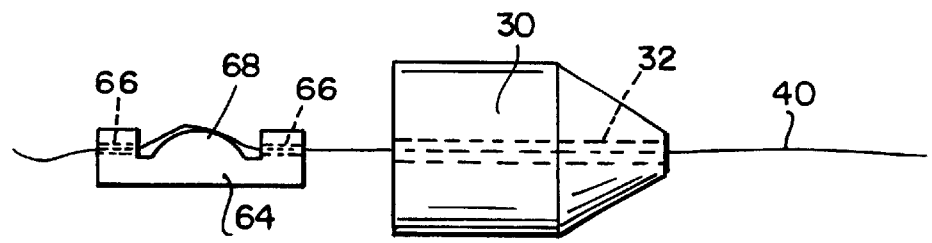
FIG. 9 is a side view of an embodiment of the inner meniscal anchor employing a wedge design.

FIG. 9 illustrates a locking mechanism employing a wedge design. Wedge 64 is generally cylindrical and is sized to fit snugly within cannula 32 of inner meniscal anchor 30. Wedge 64 is partially cannulated, defining holes 66 at either end. Suture 40 passes through holes 66 and over bulge 68. When wedge 64 is pushed along suture 40 into cannula 32, wedge 64 locks suture 40 in place.

Figure 10:
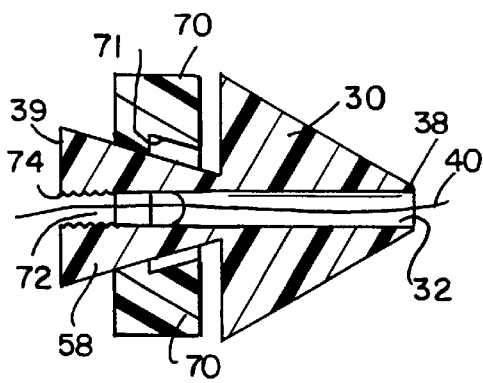
FIG. 10 is a cross section of an inner meniscal anchor with a pull locking ring.
Figure 10A:
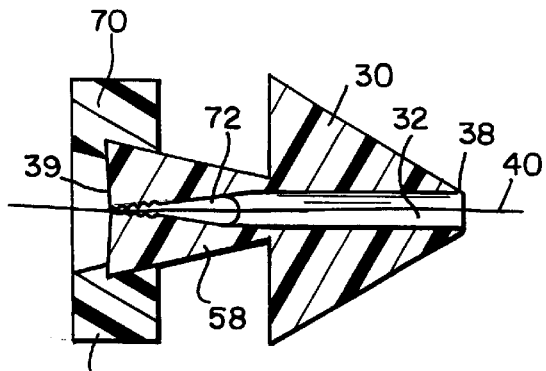
FIG. 10a is similar to FIG. 10, except showing the pull locking ring in the closed position.
Figure 11:
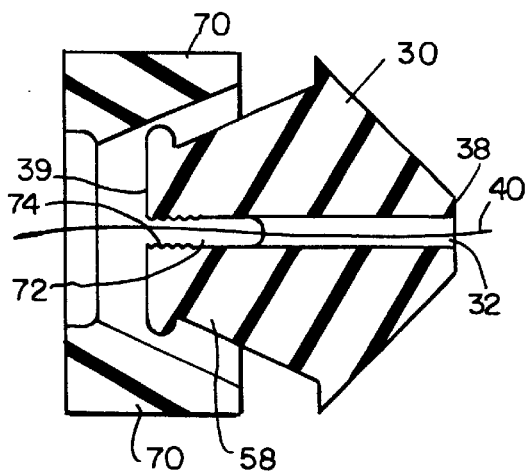
FIG. 11 is a cross section of an inner meniscal anchor with a push locking ring.

FIGS. 10 and 11 illustrate several embodiments of the inner meniscal anchor 30 which employ locking rings. FIG. 10 shows an inner meniscal anchor 30 with a pull locking ring. As with FIG. 8, rear section 58 of inner meniscal anchor 30 is provided with a split gap 72. A locking ring 70 is provided around inner meniscal anchor 30 in a position between tip 38 and end 39. After deployment of the inner meniscal anchor 30, the suture 40 is tensioned, and locking ring 70 is pulled back toward the end 39 of inner meniscal anchor 30. Locking ring 70 snaps into place when grove 71 of locking ring 70 seats around the end 39 of inner meniscal anchor 30. The locked position is illustrated in FIG. 10a. In the locked position, split gap 72 is closed, and suture 40 is pinched, thereby retained in place.

Figure 11A:
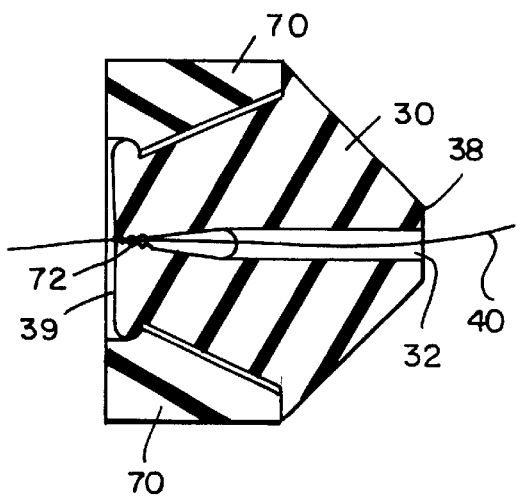
FIG. 11a is similar to FIG. 11, except showing the push locking ring in the closed position.

FIG. 11 illustrates a push type locking ring. Inner meniscal anchor 30 is again provided with a split gap 72 in the rear section 58. A locking ring 70 is provided adjacent to the end 39 of inner meniscal anchor 30. In the open position illustrated in FIG. 11, the locking ring 70 may or may not be connected to inner meniscal anchor 30. As the locking ring 70 is pushed forward toward tip 38, the locking ring squeezes rear section 58, and split gap 72 is closed. FIG. 11a illustrates the closed position. Suture 40 has become fixed within the rear section 58. As can be seen in FIGS. 10 and 11, split gap 72 may be provided with teeth 74 for better gripping of suture 40.

Figure 12:
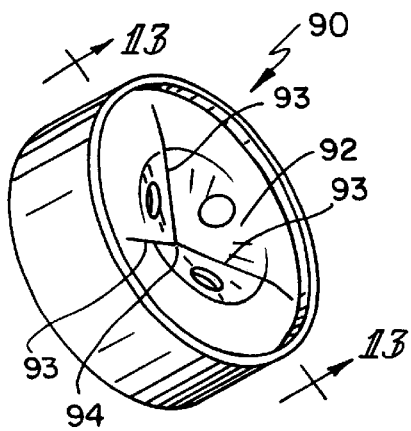
FIG. 12 is a perspective view of a locking ring of the type with laminated sheets.
Figure 13:
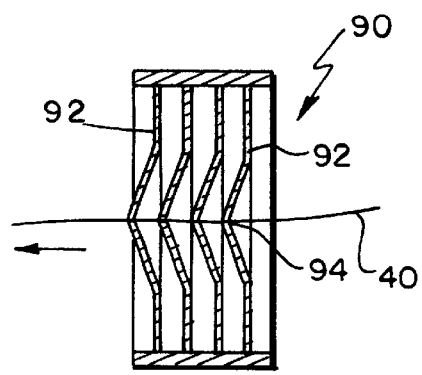
FIG. 13 is a cross section of the locking ring of FIG. 12.

FIGS. 12 and 13 illustrate another embodiment of a locking ring which may be used with this invention. Locking ring 90 is constructed from a series of laminated sheets 92. An aperture 94 is defined as the intersection of slits 93.

Aperture 94 allows suture 40 to pass through locking ring 90. As can be seen in FIG. 13, the laminated sheets are constructed such that if suture 40 is pulled in the direction indicated by the arrow, suture 40 may pass freely with little resistance. However, if suture 40 is pulled in the opposite direction, slits 93 close as laminated sheets 92 start bending back upon themselves. Thus, suture 40 is locked into position. Locking ring 90 may be used with any embodiment shown in FIGS. 3–3b, or with other embodiments of the inner meniscal anchor. Locking ring 90 may also be used as an alternative to use of an inner meniscal anchor.

Any of the locking rings may be provided as an integral component of inner meniscal anchor 30, as illustrated in FIGS. 10–11. Alternatively, the locking rings may be provided adjacent to inner meniscal anchor 30, to lock suture 40 in place adjacent to cannula 32.

Figure 14:
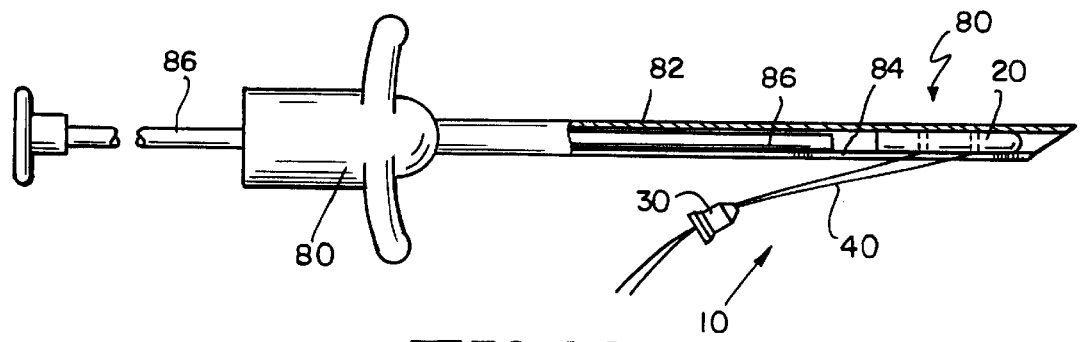
FIG. 14 is a side view of the embodiment of the meniscal repair device shown in FIG. 4, with the outer wall anchor of FIG. 2 inserted in a cannulated slotted needle, the inner meniscal anchor of FIG. 3 located outside of the needle, and the suture connecting the outer wall anchor and the inner meniscal anchor.
Figure 15:
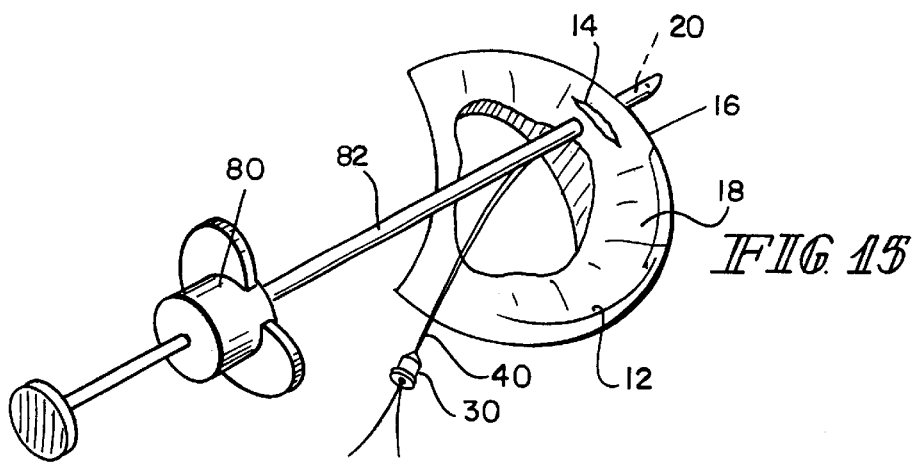
FIG. 15 is a perspective view of a meniscus having a defect, showing the needle of FIG. 14 placing the outer wall anchor adjacent to the outer meniscal wall.
Figure 16:
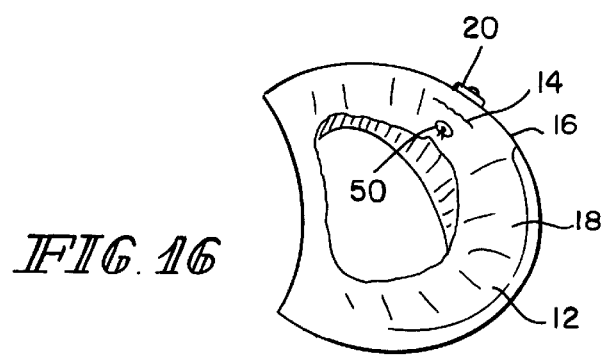
FIG. 16 is a perspective view of a meniscus showing a device of this invention approximating the defect.

FIGS. 14–16 illustrate generally a method for inserting one embodiment of the meniscal repair device 10 of this invention. Referring to FIG. 14, to insert meniscal repair device 10, outer wall anchor 20 is placed within a cannula 82 of needle 80. A slot 84 near the distal end of needle 80 allows passage of suture 40, which connects inner meniscal anchor 30 to outer wall anchor 20. Thus, only the outer wall anchor 20 need reside within needle 80, whereas the inner meniscal anchor 30 may reside on the suture 40 outside of needle 80 during deployment of outer wall anchor 20.

As illustrated in FIG. 15, the needle 80 is inserted through meniscus 12 to outer wall 16. A push rod 86 (shown in FIG. 14) placed in telescopic relation within needle 80 deploys the outer wall anchor 20 outside of meniscus 12. The outer wall anchor 20 will then flip into position, thereby disallowing the device to pull back through meniscus 12. This "flipping" is provided by locating first and second suture holes 24, 26 near the middle of outer wall anchor 20, or by providing hole 24b at or near the middle of outer wall anchor 20. With tension on suture 40, the outer wall anchor 20 provides support against the outer rim wall 16. Once the outer wall anchor 20 is deployed, a second push rod (not shown) may be used to insert the inner meniscal anchor 30 into the passageway 50 (shown in FIG. 1) created by the insertion needle 80. During insertion of the inner meniscal anchor 30, the suture 40 is held taut by the surgeon until the meniscal defect 12 is approximated. When the anchors 20, 30 are satisfactorily placed, the suture 40 may be tightened and secured, thus locking the device together and closing the defect. FIG. 16 illustrates meniscus 12 with defect 14, which has been closed by a meniscal repair device of this invention. Outer wall anchor 20 is located against the outer wall 16, while inner meniscal anchor 30 is buried within passageway 50 and is below the inner edge surface 18.

Although the invention has been described in detail with reference to certain preferred embodiments, variations and modifications exist within the scope and spirit of the invention as described and defined in the following claims.

What is claimed is:

1. A device for repairing a defect in a soft tissue comprising:
   an outer wall anchor;
   an inner anchor having a locking mechanism; and
   a suture,
   wherein the soft tissue has a first surface and a second surface and the defect is located therebetween, the suture adjustably connects the outer wall anchor to the inner anchor, the locking mechanism secures the suture to the inner anchor, and the inner anchor is shaped to seat below the first surface of the soft tissue.

2. The device of claim 1 wherein the inner anchor is cannulated and wherein the suture adjustably connects the outer wall anchor to the inner anchor by passing through the inner anchor cannulation, around the outer wall anchor, and returning through the inner anchor cannulation.

3. The device of claim 1 wherein the inner anchor is cannulated and the outer wall anchor has a hole there through, wherein the suture adjustably connects the outer wall anchor to the inner anchor by passing through the inner anchor cannulation, through the outer wall anchor hole, and returning through the inner anchor cannulation.

4. The device of claim 3 wherein the locking mechanism is a bead located on a first end of the suture to engage the returning suture in the inner anchor cannulation.

5. The device of claim 3 wherein the locking mechanism is a knot located on a first end of the suture to engage the returning suture in the inner anchor cannulation.

6. The device of claim 1 wherein the locking mechanism is a locking ring movable to secure the suture to the inner anchor.

7. The device of claim 1 wherein the soft tissue is the meniscus of a knee, the first surface is the inner surface of the meniscus, and the inner anchor is shaped to be seated below an inner surface of the meniscus.

8. The device of claim 1 wherein the inner anchor has a bullet-shape with a wide base.

9. The device of claim 1 wherein the inner anchor has a bullet shape with fins.

10. The device of claim 1 wherein the outer wall anchor is longitudinally shaped, has a pair of ends, and is formed to include a first aperture and a second aperture between the ends, the apertures for receiving the suture therethrough.

11. The outer wall anchor of claim 10 wherein the ends are squared-off.

12. The outer wall anchor of claim 10 wherein the ends are rounded.

13. (Amended) A device for connecting a soft tissue to a bone comprising:
 a bone anchor;
 a soft tissue anchor having a locking mechanism; and
 a suture,
 wherein the soft tissue has a first surface and a second surface and the second surface is adjacent to the bone, the suture adjustably connects the bone anchor to the soft tissue anchor, the locking mechanism secures the suture to the soft tissue anchor and the inner anchor is shaped to seat below the first surface of the soft tissue.

14. A device for repairing a defect in a meniscus of a knee, comprising:
 an outer wall anchor for engaging against an outside wall of the meniscus on a first side of the defect;
 an inner meniscal anchor engaging an inner surface of the meniscus on a second side of the defect, the inner meniscal anchor having a locking mechanism; and
 a suture adjustably connecting the outer wall anchor toward the inner meniscal anchor, whereby tension on the suture pulls the outer wall anchor toward the inner meniscal anchor through a continuous range of distances, thereby pulling the first and second sides of the defect together to close the defect, and the locking mechanism locks the suture in place at any point along the suture.

15. The device of claim 14 wherein the inner wall anchor is shaped to seat below the inner surface of the meniscus, whereby proper seating of the device closes the defect without interfering with tibio-femoral articulation.

16. The device of claim 15 wherein the inner wall anchor has a bullet shape to facilitate its insertion below the surface of the meniscus.

17. The device of claim 14 wherein the locking device is configured to grip and hold the suture.

18. The device of claim 14 wherein the outer wall anchor has a hole, the inner meniscal anchor is cannulated, and the suture connects the inner meniscal anchor to the outer wall anchor by passing through the inner meniscal anchor cannulation while traveling in a first direction, by passing through the outer wall anchor hole, and by returning through the inner meniscal anchor cannulation while traveling in a second and opposite direction.

19. A method for repairing a defect in a meniscus, comprising the steps of:
 providing a meniscal repair device comprising an outer wall anchor for engaging against an outside wall of the meniscus on a first side of the defect; an inner meniscal anchor for engaging an inner surface of the meniscus on a second side of the defect, the inner meniscal anchor having a locking mechanism; and a suture adjustably connecting the outer wall anchor to the inner meniscal anchor;
 providing a cannulated needle having a push rod;
 placing the outer wall anchor within the cannulated needle;
 inserting the cannulated needle into the meniscus from an inner surface of the meniscus, through the defect, to the outside wall of the meniscus;
 deploying the outer wall anchor with the push rod;
 pushing the inner meniscal anchor into the inner surface of the meniscus;
 tensioning the suture to pull the first and second sides of the defect together; and
 locking the suture in place with the locking mechanism.

20. The method of claim 19 further comprising the step of:
 pulling on the suture to seat the outer wall anchor against the outside wall of the meniscus once the outer wall anchor has been deployed.

21. The method of claim 19 wherein the suture connects the inner meniscal anchor to the outer wall anchor by passing through the inner meniscal anchor cannulation while traveling in a first direction, around the outer wall anchor, and returning through the inner anchor cannulation.

22. The method of claim 21 wherein the locking mechanism is a bead located on a first end of the suture to engage the returning suture in the inner anchor cannulation.

23. The method of claim 21 wherein the locking mechanism is a knot located on a first end of the suture to engage the returning suture in the inner anchor cannulation.

24. The method of claim 19 wherein the locking mechanism is a locking ring moveable to secure the inner anchor.

25. The method of claim 19 wherein the inner anchor is shaped to be seated below the surface of a region of soft tissue adjacent to the soft tissue defect and the pushing step seats the inner anchor below the inner surface of the meniscus.

26. The method of claim 25 wherein the inner anchor is bullet-shaped with a wide base.

27. The method of claim 25 wherein the inner anchor has a bullet-shape with fins.

28. The method of claim 25 wherein the outer wall anchor is a torus and the outer wall anchor promotes pulley action in the tensioning step.

29. A device for repairing a soft tissue defect comprising:
 an outer wall anchor;

an inner anchor having a locking mechanism; and a suture, wherein the suture adjustably connects the outer wall anchor to the inner anchor and the locking mechanism secures the suture to the inner anchor, and the outer wall anchor is an elongated torus formed to include an aperture for receiving the suture.

30. The outer wall anchor of claim 29 wherein the aperture is located off-center.

31. A device for repairing a defect in a meniscus of a knee, comprising:

an outer wall anchor for engaging against an outside wall of the meniscus on a first side of the defect, an inner meniscal anchor for engaging an inner surface of the meniscus on a second side of the defect, the inner meniscal anchor having a locking mechanism; and a suture adjustably connecting the outer wall anchor to the inner meniscal anchor;

wherein the outer wall anchor has a hole therethrough, the inner meniscal anchor is cannulated, and the suture connects the inner meniscal anchor to the outer wall anchor by passing through the inner meniscal anchor cannulation while traveling in a first direction, by passing through the outer wall anchor hole, and by returning through the inner meniscal anchor cannulation while traveling in a second and opposite direction and wherein tension on the suture pulls the outer wall anchor toward the inner meniscal anchor, thereby pulling the first and second sides of the defect together to close the defect, and the locking mechanism locks the suture in place.

* * * * *